United States Patent [19]

Shouldice et al.

[11] Patent Number: 4,897,184
[45] Date of Patent: Jan. 30, 1990

[54] FLUID FLOW APPARATUS CONTROL AND MONITORING

[75] Inventors: David R. Shouldice, Lakewood; Daniel A. Powell; Tom L. Brose, both of Littleton, all of Colo.

[73] Assignee: Cobe Laboratories, Inc., Lakewood, Colo.

[21] Appl. No.: 925,305

[22] Filed: Oct. 31, 1986

[51] Int. Cl.[4] ............................................. B01D 13/00
[52] U.S. Cl. ...................................... 210/87; 210/90; 210/96.2; 210/143
[58] Field of Search ..................... 210/85, 87, 90, 96.2, 210/143

[56] References Cited

U.S. PATENT DOCUMENTS

| | | | |
|---|---|---|---|
| 3,946,731 | 3/1976 | Lichtenstein | 210/87 |
| 4,153,554 | 5/1979 | Heide et al. | 210/96.2 |
| 4,370,983 | 2/1983 | Lichtenstein | 210/321.2 |
| 4,371,385 | 2/1983 | Johnson | 55/190 |

Primary Examiner—Frank Spear

[57] ABSTRACT

Dialysate preparation apparatus including dialysate and blood flow lines connected to a dialyzer, fluid control mechanisms on the lines to control conditions of fluid in the lines, fluid condition sensors on the lines to sense the conditions of fluid in the lines, a digital control processor receiving signals from the sensors and controlling the mechanism to achieve desired fluid conditions, and the digital monitor processor receiving signals from the sensors and verifying that fluid conditions meet predetermined safety limits.

14 Claims, 2 Drawing Sheets

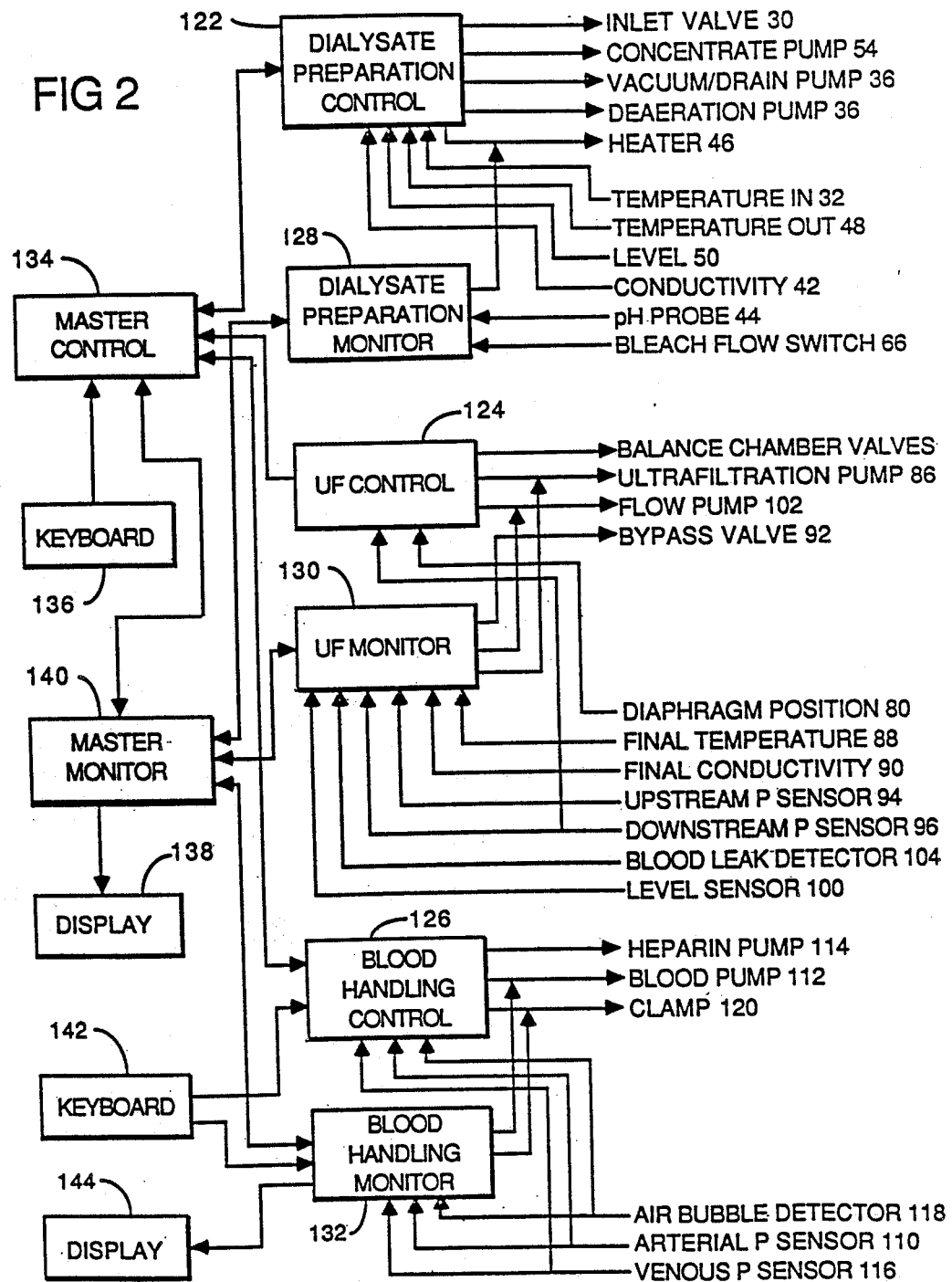

FLUID FLOW APPARATUS CONTROL AND MONITORING

FIELD OF THE INVENTION

The invention relates to automatic control and monitoring of fluid conditions in fluid flow apparatus.

BACKGROUND OF THE INVENTION

In fluid flow apparatus, for example dialysate preparation and supply machines, fluid conditions (e.g., fluid composition, temperature, pressure, and flow rate) are controlled by various control mechanisms (e.g., pumps, heaters, valves, and pressure regulators) and are monitored by fluid condition sensors (e.g., conductivity, pH, level, temperature, pressure, air bubble, and blood sensors). The fluid condition sensors are used both to control the various fluid control mechanisms so as to achieve desired fluid conditions and to monitor the conditions to make sure that they are within safe limits.

In some prior art dialysate preparation and supply machines, the monitoring and control functions are both carried out by a digital processor, and there is on-line verification that the monitoring function is operating correctly. Another prior art dialysate machine approach involves using a digital processor to control the fluid conditions, and analog circuits to monitor the conditions to make sure that safety limits are met.

SUMMARY OF THE INVENTION

We have discovered that by using a digital control processor to control fluid conditions based upon signals received from sensors and a separate digital monitor processor to verify that fluid conditions meet predetermined safety limits, we would have reliable digital safety monitoring in the event of control processor malfunction, and the safety limits could be automatically adjusted in response to changes in operating conditions set by the operator. In the preferred embodiment, there are a plurality of pairs of digital control processors and digital monitor processors (each pair being assigned to a hydraulic subsystem of the fluid flow apparatus), a master control processor communicating with the subsystem control processors, and a master monitor processor communicating with the subsystem monitor processors.

The preferred apparatus is dialysate preparation and supply apparatus including a blood flow line for flow of blood between a patient and a dialyzer and a dialysate flow line for flow of dialysate to and from the dialyzer; the apparatus includes a bypass valve operable to direct dialysate to a bypass line that bypasses the dialyzer upon the existence of temperature or conductivity conditions outside of predetermined safety limits; there is a clamping valve on the blood flow line operable to block flow of blood through it upon the detection of air bubbles in the blood line downstream of the dialyzer; a blood pump and an ultrafiltration pump are turned off if blood is detected in the dialysate line downstream of the dialyzer (indicating a membrane leak in the dialyzer); the transmembrane pressure is monitored and used to turn off an ultrafiltration pump when transmembrane pressure exceeds a predetermined limit; and blood pressure sensors are used to turn off a blood pump if the pressures sensed are too high, indicating a block in the line, or too low, indicating a disconnected line.

Other features and advantages of the invention will be apparent from the following description of the preferred embodiment thereof and from the claims.

DESCRIPTION OF THE PREFERRED EMBODIMENT

The preferred embodiment will now be described.

DRAWINGS

FIG. 2 is a block diagram of digital control and monitor processors used to control the FIG. 1 apparatus according to the invention.

STRUCTURE

Figure 1:
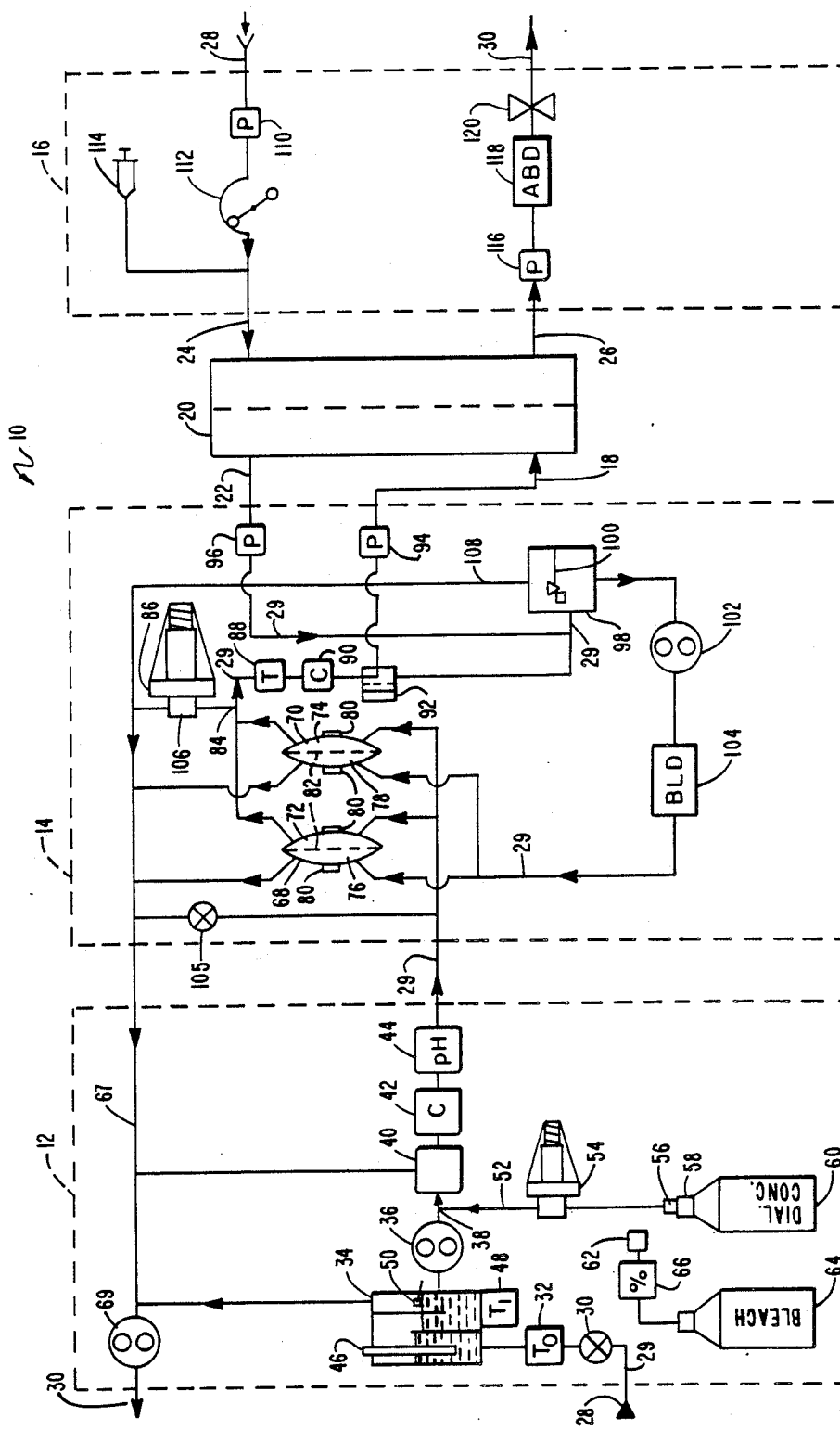
FIG. 1 is a schematic representation of dialysate preparation and supply apparatus according to the invention.

Referring to FIG. 1, there is shown dialysate preparation and supply apparatus 10 including dialysate preparation subsystem 12, ultrafiltration control (UFC) subsystem 14, and blood-handling subsystem 16. Dialysate is supplied from UFC subsystem 14 to dialysate inlet 18 of dialyzer 20, having a pleated membrane therein defining dialysate channels on one side of it and blood channels on its other side. Spent dialysate is returned to UFC subsystem 14 from dialysate outlet 22 of dialyzer 20. Blood is supplied to blood inlet 24 of dialyzer 20 from blood-handling subsystem 16 and is returned to subsystem 16 from blood outlet 26 of dialyzer 20. A patient is connected to blood supply line 28 and blood return line 30 of blood handling subsystem 16.

Dialysate preparation subsystem 12 receives tap water at inlet 28 and discharges spent dialysate at drain 30. Downstream from inlet 28 along main flow line 29 are on/off solenoid valve 30, temperature sensor 32, heater/deaeration chamber 34, deaeration gear pump 36, junction 38 (at which concentrate is added), mixing chamber 40, conductivity sensor 42, and pH sensor 44. Heater/deaeration chambr 34 includes 800-watt immersion heater 46, temperature sensor 48 (sensing temperature of water leaving the heater), and level sensor 50. Connected to junction 38 is concentrate line 52, including concentrate pump 54 (a constant-stroke-volume diaphragm pump) and fitting 56 on its remote end for connecting to either fitting 58 of dialysate concentrate jug 60 or fitting 62, connected to bleach jug 64 via a line including flow sensing switch 66. Air separation lines from heater/deaeration chamber 34 and mixing chamber 40 are connected to vacuum/waste line 67 leading to vacuum/waste gear pump 69.

UFC subsystem 14 includes, continuing along main flow line 29, balance chambers 68, 70, connected in parallel and having fresh dialysate chambers 72, 74 on the right-hand sides and spent dialysate chambers 76, 78 on the left-hand sides. Hall effect sensors 80 sense the positions of magnets carried by the diaphragms 82 in balance chambers 68, 70. Downstream of the fresh dialysate chambers of balance chambers 68, 70 are junction 84 (to ultrafiltration pump 86, a constant-stroke-volume diaphragm pump), final temperature sensor 88, final conductivity sensor 90, two-position bypass valve 92, and dialysate inlet pressure sensor 94, just upstream of dialysate inlet 18. Downstream of dialyzer 20 in the UFC subsystem are dialysate outlet pressure sensor 96, air separator 98 (including level sensor 100 therein), gear flow pump 102, and blood leak detector 104, just upstream of spent dialysate chambers 76, 78 of balance chambers 68, 70. The outlets of spent dialysate chambers 76, 78 are connected to vacuum/waste line 67 leading to vacuum/waste pump 69, as are the waste line from ultrafiltration pump 86 and air separation line 108 from air separator 98. Balance chambers 68, 70 have solenoid valves connected to the inlets and outlets to alternately fill a fresh dialysate chamber while the spent dialysate chamber of the same balance chamber is being emptied and to fill the spent dialysate chamber of the other balance chamber with spent dialysate while its fresh dialysate chamber is being emptied, and vice versa, as is known in the art. In this manner, dialysate flow to and from dialyzer 20 is balanced, and the precise amount of ultrafiltrate (liquid passing through the membrane in dialyzer 20 from blood to dialysate) is removed, by removing the desired amount using pump 86. Two-position bypass valve 92 includes the flow path shown at the right of the dashed line, connecting main flow line 29 to the dialyzer, and the flow path shown at the left of the dashed line, bypassing dialyzer 20.

Blood-handling subsystem 16 includes arterial pressure sensor 110, peristaltic blood pump 112, and heparin pump 114 on blood supply line 28 from the patient to blood inlet 24. It also includes venous pressure sensor 116, air bubble detector 118, and solenoid clamping valve 120 on blood return line 30 from blood outlet 26 to the patient.

Referring to FIG. 2, there is shown the block diagram for the control and monitoring system of apparatus 10. Each hydraulic subsystem 12, 14, 16 has a corresponding digital control processor 122, 124, 126 and a corresponding digital monitor processor 128, 130, 132, respectively. Each control processor 122, 124, 126 is connected to master controller 134, connected to receive operator input from data entry keyboard 136. Each digital monitor 128, 130, 132 is similarly connected to a master monitor processor 140, connected to communicate information to the operator via CRT display 138. The blood handling system also has its own data entry keyboard 142 and LED display 144 connected as shown in FIG. 2. As is also shown in FIG. 2, the control and monitor processors are connected to receive fluid condition signals from the indicated fluid condition sensors, and the control processors are connected to provide control signals to the indicated control mechanisms. In some instances, the fluid condition sensors are connected to both the control processor and the monitor processor in a subsystem. In some instances the monitor processors can remove the power from control mechanisms. The digital control and monitor processors are programmed to carry out the control and monitoring functions described below.

OPERATION

In operation, dialysate is continuously prepared in dialysate preparation subsystem 12 and supplied to and removed from the dialysate passages in dialyzer 20 at controlled flow rates by UFC subsystem 14, and blood is continuously supplied to and removed from the blood passages of dialyzer 20. The control of fluid conditions by each subsystem will be discussed first, and this will be followed by discussion of safety condition monitoring. Unless otherwise indicated, the fluid control mechanisms (i.e., the pumps, valves, etc.) are controlled by control loops carried out by the digital control processors of the respective hydraulic subsystems.

In dialysate preparation subsystem 12, water enters inlet 28, is heated and deaerated in chamber 34, and receives dialysate concentrate at junction 38. The mixed dialysate then flows to UFC subsystem 14. Heater 46 is switched on and off based upon the inlet and outlet temperatures sensed by temperature sensors 32, 48. Valve 30 is switched on and off in a six-second on/off duty cycle based upon the level of liquid sensed by level sensor 50. Concentrate pump 54 is controlled by the conductivity sensed by conductivity sensor 42. Deaeration pump 36 and vacuum/waste pump 69 are also controlled by control processor 122 to achieve desired flow rates, which can be entered into master controller 134 by the operator.

In UFC subsystem 14, dialysate flows alternately into and out of fresh dialysate chambers 72, 74 (one being filled while the other is emptied), flows through the dialysate passages of dialyzer 20, flows alternately into and out of spent dialysate chambers 76, 78 (one being filled while the other is emptied), and flows to vacuum/waste line 67. The balance chamber valves (not shown) at the inlets and outlets of balance chambers 68, 70 are switched open or shut in response to signals from diaphragm position sensors 80 indicating the end of travel of the diaphragms. When a frsh dialysate chamber has been filled, but the fresh dialysate chamber being emptied at that time has not finished emptying, dump valve 105 dumps incoming dialysate until the last mentioned chamber has been emptied, so that the flow from dialysate preparation subsystem 12 will not be disrupted. Ultrafiltration pump 86 is controlled by control processor 124 to pump liquid out at a rate equal to desired ultrafiltration entered into the master control processor 134 by the operator. Flow pump 102 is similarly controlled based upon desired flow rate entered into master control processor 134.

In blood-handling subsystem 16, blood is pumped from the patient by blood pump 112 at a desired flow rate, and heparin is pumped by heparin pump 114 at a desired flow rate, both under the control of blood handling control processor 126, based upon desired flow rates entered into keyboard 136 and keyboard 142, respectively, and by the operator.

Monitor processors 128, 130, 132 simultaneously monitor the conditions sensed by their respective sensors to verify that safety limits are met. If not, audible and visual alarms are given (even if not specifically mentioned below), and various precautionary measures are typically taken (as indicated below) to avoid harming the patient.

In dialysate preparation subsystem 12, bleach flow switch 66 is used to verify that apparatus 10 is in a cleaning or disinfecting mode when flow switch 66 senses flow through it, to guarantee that bleach will not be pumped into the system when it is connected to a patient in the dialysis mode. If switch 66 senses flow when in the dialysis mode, or if pH sensor probe 44 senses that the pH is not within safe limits corresponding to pH associated with desired dialysate composition, dialysate preparation monitor 128 communicates these conditions via master monitor processor 140 to UF monitor processor 130, which then pulls power to UF pump 86 and flow pmp 102 and activates bypass valve 92, bypassing flow around dialyzer 20.

In UFC subsystem 14, final temperature sensor 88 has a maximum temperature associated with it, and final conductivity sensor 90 has upper and lower conductivity limits associated with it. If either condition is violated, bypass valve 92 is activated. If blood leak detector 104 senses the presence of blood, this condition is communicated via ultrafiltration monitor processor 130 to master monitor processor 140, which tells blood handling monitor processor 132 to turn off blood pump 112 and communicates the condition via master control processor 134 to UF control processor 124, which operates to bring transmembrane pressure to zero. A transmembrane pressure that is too high, sensed by signals from both UF monitor processor 130 and blood handling monitor processor 132, triggers a similar response. A TMP that is too high indicates that the operator is trying to pull too much ultrafiltrate (in which event he can lower the ultrafiltration rate) or that the membrane is clogged (in which event use of the clogged dialyzer must be discontinued). One possible response to a detected blood leak condition is increasing the triggering value of the blood leak detector. Level sensor 100 will shut off flow pump 102 if the level in it gets so low that pump 102 could begin to suck air through it.

Blood pressure sensors 110, 116 measure the pressure in the blood supply and return lines. If pressure in one of these lines is too high, indicating a blocked condition, or too low, indicating a disconnected line, blood pump 112 is turned off by pulling the power to it, and an alarm is sounded. If air bubble detector 118 detects the presence of an air bubble, blood handling monitor processor 132 and/or blood handling control processor 126 will block blood flow to the patient, using clamp 120, and will turn off blood pump 112, by pulling the power to these control mechanisms. If air bubble detector 118 fails, the signal provided to the processors will be the same as if it had detected an air bubble, thus preventing a single failure from undermining the safety system.

OTHER EMBODIMENTS

Other embodiments of the invention are within the scope of the following claims.

What is claimed is:

1. Dialysate preparation and supply apparatus comprising,
    a dialyzer,
    a blood flow line for flow of blood between a patient and said dialyzer,
    a dialysate flow line for flow of dialysate to and from said dialyzer,
    at least one fluid control mechanism means on a said line for control fluid conditions in said line,
    at least one fluid condition control sensor means on a said line for sensing a condition of fluid in said line,
    a plurality of fluid condition monitor sensors means for sensing conditions of fluid in a said line,
    at least one fluid condition monitor sensor means on said line sensing the same said condition of fluid in said line as a said fluid condition control sensor,
    at least one digital control processor means for receiving signals from said control sensor means and controlling a said fluid control mechanism means to achieve a desired fluid condition,
    at least one digital monitor processor means for receiving signals directly from said monitor sensor means and verifying that said fluid condition sensed by said monitor sensor means meets a predetermined safety limit,
    means for safeguarding said patient if said fluid condition sensed does not meet said predetermined safety limit,
    a digital master control processor means for communicating with said at least one digital control processor means, and
    a digital master monitor processor means for communicating with said at least one digital monitor processor means.

2. The apparatus of claim 1 further comprising a bypass line that is connected to said dialysate flow line so as to bypass said dialyzer, and wherein said means for safeguarding includes a bypass valve operable to direct dialysate to said bypass line to bypass said dialyzer, said bypass valve being connected to receive a bypass signal from said monitor processor means.

3. The apparatus of claim 2 wherein at least one said fluid condition monitor sensor means includes a first conductivity sensor mounted to sense conductivity of dialysate in said dialysate line upstream of said dialyzer, said first conductivity sensor being connected to provide a conductivity signal to said digital monitor processor means, said digital monitor processor means being programmed to provide said bypass signal when conductivity does not meet a predetermined conductivity safety limit and wherein at least one said fluid condition control sensor means comprises a second conductivity sensor mounted to sense conductivity of dialysate in said dialysate line.

4. The apparatus of claim 2 wherein at least one said fluid condition monitor sensor means includes a first temperature sensor means mounted to sense temperature of dialysate in said dialysate line upstream of said dialyzer, said first temperature sensor means being connected to provide a temperature signal to said monitor processor means, said monitor processor means beng programmed to provide said bypass signal when temperature does not meet a predetermined temperature safety limit and wherein at least one said fluid condition control sensor means comprises a second temperature sensor means mounted to sense temperature of dialysate in said dialysate line.

5. The apparatus of claim 1 wherein said means for safeguarding includes a clamping valve means on said blood flow line operable to selectively block flow of blood through said line, said clamping valve means being connected to receive a blocking signal from said monitor processor means.

6. The apparatus of claim 5 wherein at least one said fluid condition monitor sensor means includes an air bubble detector means mounted on said blood line downstream of said dialyzer, said air bubble detector means being connected to provide an air bubble signal to said digital monitor processor means, said monitor processor means being programmed to provide said blocking signal when air bubbles are detected.

7. The apparatus of claim 1 wherein at least one said fluid control mechanism means includes a blood pump means on said blood flow line, said blood pump means being connected to receive control signals indicating desired blood flow rate from said digital control processor means, and to receive a blood pump turn-off signal from said digital monitor processor means.

8. The apparatus of claim 7 wherein at least one said fluid condition monitor sensor includes an air bubble detector means mounted on said blood line downstream of said dialyzer, said air bubble detector being connected to provide an air bubble signal to said monitor processor means, said monitor processor means being programmed to provide said blood pump turn-off signal when air bubbles are detected.

9. The apparatus of claim 7 wherein at least one said fluid condition monitor sensor means includes a blood leak detector means mounted on said dialysate line downstream of said dialyzer, said blood leak detector means being connected to provide a blood leak signal to said digital monitor processor means, said digital monitor processor means being programmed to provide a blood pump turn-off signal when a blood leak is detected.

10. The apparatus of claim 7 wherein at least one said fluid condition monitor sensor means includes a blood pressure sensor means on said blood line, said blood pressure sensor means is connected to provide a blood pressure signal to said digital monitor processor means, and said digital monitor processor means is programmed to provide said blood pump turn-off signal when blood pressure does not meet a predetermined safety limit.

11. The apparatus of claim 10 wherein at least one said fluid condition monitor means includes a dialysate pressure sensor means on said dialysate line, said dialysate pressure sensor means being connected to provide a dialysate pressure signal to said digital monitor processor means, and said digital monitor processor means being programmed to provide said blood pump turn-off signal when the transmembrane pressure does not meet a predetermined transmembrane pressure safety limit.

12. The apparatus of claim 11 wherein at least one said fluid control mechanism means includes an ultrafiltration pump means on said dialysate line, said ultrafiltration pump means being connected to receive control signals indicating desired ultrafiltration rate from said digital control processor means and to receive an ultrafiltration pump turn-off signal from said digital monitor processor means, said digital monitor processor means being programmed to provide said ultrafiltration pump turn-off signal when the transmembrane pressure does not meet a predetermined transmembrane pressure safety limit.

13. The apparatus of claim 1 wherein said apparatus has a plurality of hydraulic subsystems, and each said hydraulic subsystem includes at least one fluid control mechanism means, at least one fluid condition sensor means, a digital control processor means receiving signals from at least one said fluid condition sensor in each said subsystem and controlling said control mechanism means in each said subsystem to achieve a desired fluid condition, and a digital monitor processor means receiving signals from said sensor in each said subsystem and verifying that a said fluid condition meets a predetermined safety limit, and further comprising a digital master control processor means for communicating with said digital control processor means of said plurality of subsystems and a digital master monitor processor means communicating with said digital monitor processor means of said plurality of subsystems.

14. Dialysate preparation and supply apparatus comprising a dialyzer, a blood flow line for flow of blood between a patient and said dialyzer, a dialysate flow line for flow of dialysate to and from said dialyzer, at least one fluid control mechanism means on a said line for controlling fluid conditions in said line, at least one fluid condition control sensor means on a said line for sensing a condition of fluid in said line, at least one fluid condition monitor sensor means on said line sensing a condition of fluid in said line, a digital control processor means for receiving signals from said control sensor means and controlling a said fluid control mechanism means to achieve a desired fluid condition, a digital monitor processor means for receiving signals directly from said monitor sensor means and verifying that said fluid condition sensed by said monitor sensor means meets a predetermined safety limit, and means for safeguarding said patient if said fluid condition sensed does not meet said predetermined safety limit, said fluid condition monitor sensor means sending the same signal to said digital monitor processor means, when failing, that it does when it detects a fluid condition not meeting said predetermined safety limits, thereby preventing a single failure from undermining the safety system.

* * * * *